(12) United States Patent
Blomberg et al.

(10) Patent No.: US 7,634,311 B2
(45) Date of Patent: Dec. 15, 2009

(54) METHOD, DEVICE AND COMPUTER PROGRAM PRODUCT FOR FILTERING AN EMG SIGNAL OUT OF A RAW SIGNAL

(75) Inventors: Urban Blomberg, Solna (SE); Fredrik Jalde, Bromma (SE)

(73) Assignee: Maquet Critical Care AB, Solna (SE)

( * ) Notice: Subject to any disclaimer, the term of this patent is extended or adjusted under 35 U.S.C. 154(b) by 117 days.

(21) Appl. No.: 10/579,314

(22) PCT Filed: Nov. 18, 2004

(86) PCT No.: PCT/SE2004/001689

§ 371 (c)(1),
(2), (4) Date: May 16, 2006

(87) PCT Pub. No.: WO2005/048838

PCT Pub. Date: Jun. 2, 2005

(65) Prior Publication Data

US 2007/0129915 A1    Jun. 7, 2007

(30) Foreign Application Priority Data

Nov. 19, 2003    (SE)    .................................... 0303062

(51) Int. Cl.
*A61B 5/04*    (2006.01)
*H03F 1/26*    (2006.01)
*H04B 15/00*    (2006.01)

(52) U.S. Cl. ........................ 600/546; 600/509; 702/191
(58) Field of Classification Search .................. 600/546, 600/509; 702/191
See application file for complete search history.

(56) References Cited

U.S. PATENT DOCUMENTS

| | | | |
|---|---|---|---|
| 4,248,240 A | 2/1981 | Van Eykern | |
| 5,671,752 A | 9/1997 | Sinderby et al. | |
| 5,820,560 A | 10/1998 | Sinderby et al. | |
| 6,901,286 B1 * | 5/2005 | Sinderby et al. | ............ 600/546 |

FOREIGN PATENT DOCUMENTS

WO    WO 01/03579    1/2001

* cited by examiner

*Primary Examiner*—Max Hindenburg
*Assistant Examiner*—Emily M Lloyd
(74) *Attorney, Agent, or Firm*—Schiff Hardin LLP

(57) ABSTRACT

In a method, device and computer program product for extracting an EMG signal out of a raw signal obtained with a number of electrodes, the electrodes being adapted to interact with a patient to obtain signals from the patient's diaphragm on respective channels associated with the electrodes, a signal-to-noise-ratio is determined for the raw signal in each channel, and a weighting factor is automatically determined dependent on the signal-to-noise ratio. The respective raw signals from the channels are weighted according to the weighting factors, and are summed in order to generate a sum signal that represents the total EMG signal contained in all of the raw signals.

18 Claims, 7 Drawing Sheets

METHOD, DEVICE AND COMPUTER PROGRAM PRODUCT FOR FILTERING AN EMG SIGNAL OUT OF A RAW SIGNAL

BACKGROUND OF THE INVENTION

1. Field of the Invention

The present invention concerns a method, device and computer program product for the purpose of filtering an EMG signal out of a raw signal, i.e., for extracting an EMG signal from a raw signal that contains the EMG signal, among other signal components.

2. Description of the Prior Art

Sensing of EMG-signals in a patient's diaphragm by placing a catheter with a number of electrodes in the esophagus is a known technique, which is described in, among others, U.S. Pat. No. 5,671,752. The EMG-signals received can be used in connection with mechanical ventilation of patients, which among others is described in U.S. Pat. No. 5,820,560 and WO 98/48877.

Sensing of EMG-signals from the diaphragm can even take place outside the body with electrodes placed on the patient, such as described in e.g. U.S. Pat. No. 4,248,240.

If a catheter with electrodes is guided down in the esophagus the electrodes lie on both sides of the diaphragm and at different distances therefrom. Each electrode's position relative to the diaphragm is normally not known and furthermore can vary when the patient breathes or moves in another way.

Since the EMG-signal from the diaphragm is relatively weak, in particular compared to interferences from EKG, a continuous desire is to in the best way attain the highest quality possible signal handling of the raw signal which the sensors detect. This is evident even in WO 01/03579. In WO 01/03579 it is assumed that the electrodes' location in relation to the center of the diaphragm is known. Then the electrodes are weighted based on location and symmetry, in which the EKG signal is taken into account in a conventional way.

Known methods for compensating for the EKG signal include, among others, using a band pass filter which filters out the frequencies where the EKG signal normally appears. It is also known to measure the EKG signal separately and then remove an equivalent signal from the measured EMG signal.

None of these methods takes into account the actual disturbance the EKG signal creates in a particular measuring situation in a particular patient. This disturbance also varies with time.

The known methods also fail to consider that the electrodes location relative to the diaphragm often varies during a single measurement.

SUMMARY OF THE INVENTION

An object of the present invention is to provide a method and a device and a computer program product for measuring EMG signals that take into consideration that the location of the electrodes varies during a measurement.

The above object is achieved in accordance with the present invention by a method, device and a computer program product (i.e., a computer-readable medium encoded with computer program data) wherein a raw signal is obtained from a number of electrodes that are adapted for placement in a patient to capture signals from the patient's diaphragm, each electrode having an associated signal channel, wherein a signal-to-noise ratio is determined for each signal channel and a weighting factor is generated for each signal channel based on the signal-to-noise ratio, and the channels are summed dependent on the weighting factors.

By selectively estimating the signal-to-noise ratio for each signal channel and arranging significance factors depending upon the signal-to-noise ratio, the channels with the highest quality can be used more effectively for determining the EMG-signal.

Since EKG-signals constitute a primary disturbance source, the determination can in large part be done in relation to these signals. The signal-to-noise ratio can then be determined as the quotient between an estimated EKG-activity and an estimated EMG-activity. The quotient can be determined so that a high estimated EMG-activity is always awarded, e.g. by applying the equation $$\frac{R^2}{R+S}$$

where R represents the EMG-activity and S represents the EKG-activity.

DESCRIPTION OF THE PREFERRED EMBODIMENTS

The signal and raw signal are defined to encompass n-1 signals from the n electrodes/sensors, and for the n-1 signals there are n-1 channels.

Figure 1:
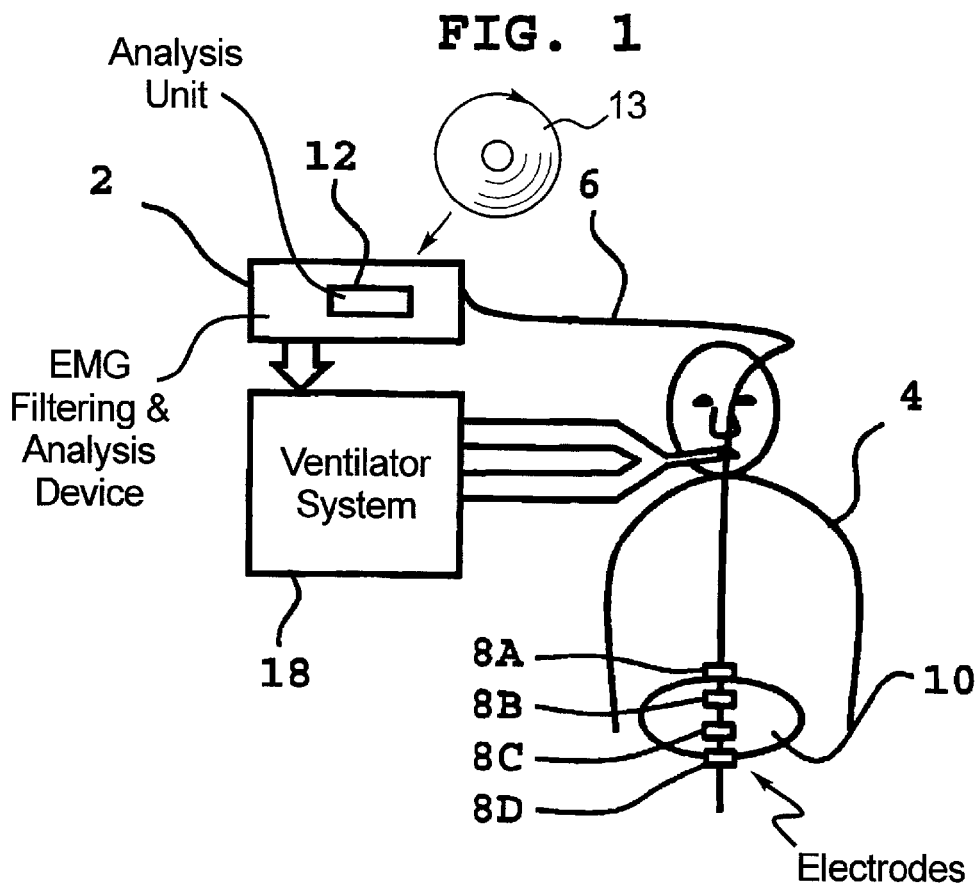
FIG. 1 shows a device according to the invention connected to a patient who is undergoing respiratory therapy.

FIG. 1 shows a device 2 for filtering and analysis of EMG-signals according to the invention. The device 2 can in a known way be connected to a patient 4 via a catheter 6 with a number of electrodes 8A, 8B, 8C, 8D in one end (four electrodes are shown, but the number can be larger or smaller). By placing the catheter 6 in the esophagus of the patient 4, the electrodes 8A, 8B, 8C, 8D can be placed in different locations in the diaphragm 10 (the size of which has been exaggerated in FIG. 1 to indicate the relative placement of the electrodes 8A, 8B, 8C, 8D). In an analysis unit 12 in the device 2, filtering and analysis of the raw signal from the catheter 6 is done to extract the highest quality EMG-signal possible.

Figure 2:
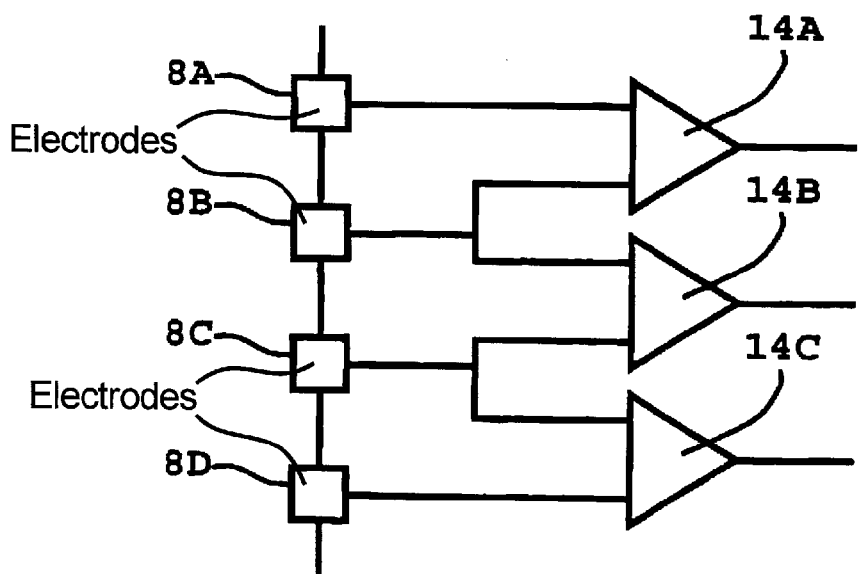
FIG. 2 shows a first example of electrode coupling for receiving a raw signal.
Figure 3:
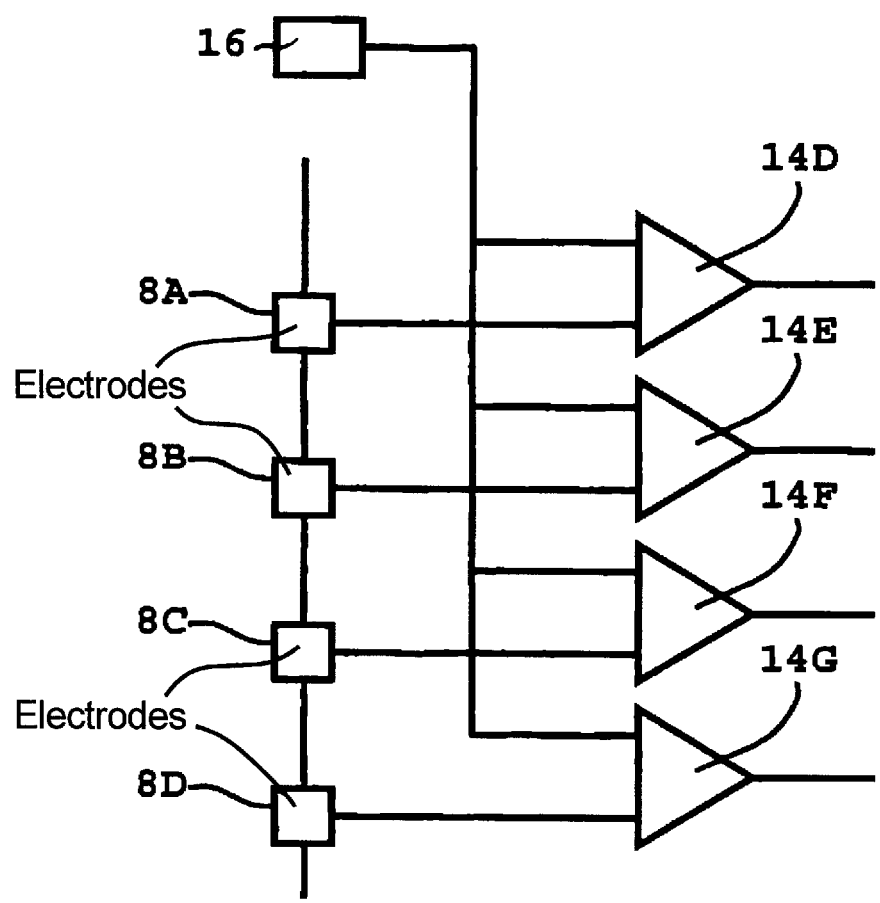
FIG. 3 shows a second example of electrode couplings for receiving a raw signal.

In this connection, the raw signal can be received in many different ways. FIGS. 2 and 3 show two embodiments. From FIG. 2 it is evident that the electrodes 8A, 8B, 8C, 8D are coupled together in pairs via three couplers 14A, 14B, 14C and in that way give rise to a three-channel raw signal (with e.g. nine electrodes, eight channels are received).

In FIG. 3 an example is shown where the respective electrodes 8A, 8B, 8C, 8D are connected to a reference electrode 16 (which e.g. can be grounded) via four couplers 14D, 14E, 14F, 14G. This results in a four-channel raw signal (for eight channels in this arrangement, eight electrodes and one reference are required).

Naturally an arbitrary number of electrodes can be used and for n electrodes, n-1 signals are allowed, and thereby n-1 channels.

More information regarding the catheter, the sensors and the entire process to capture raw signals from the diaphragm via esophagus can be found in e.g. U.S. Pat. No. 5,671,752 and WO 01/03579. As already noted, electrodes connected outside the body can even be used instead, for completely non-invasive reception of EMG-signals.

The patient 4 can also be connected in conventional ways to a ventilator system 18, which in turn can be connected to the device 2 via a suitable connection 20. The respiratory therapy given via the ventilator system 18 in that way can be influenced by the EMG-signal, which is extracted from the raw signal from the diaphragm 10. This influence can be done in many different ways, of which some are described in U.S. Pat. No. 5,820,560 and WO 99/43374.

The present invention is directed to the device 2 and, to be precise, the analysis unit 12. The analysis unit 12 filters EMG-signals out of the raw signal from the catheter 6. The analysis unit can be operated by a computer program encoded on a computer-readable medium, such as a CD-ROM 13. In that connection a number of signal channels are used, as noted above.

To receive the highest quality possible in the EMG-signals, the raw signal contains in addition to EMG even EKG, alternating current noise, noise, movement artifacts and other low frequency disturbances, filtering in the analysis unit 12 is done according to the method described below, which can be performed in an analog or digital manner, or as a combination thereof and can be realized in hardware, software or in a combination thereof.

The method is described in connection with the flowcharts in FIGS. 4, 5, 6, 7, 8 and 9.

Figure 4:
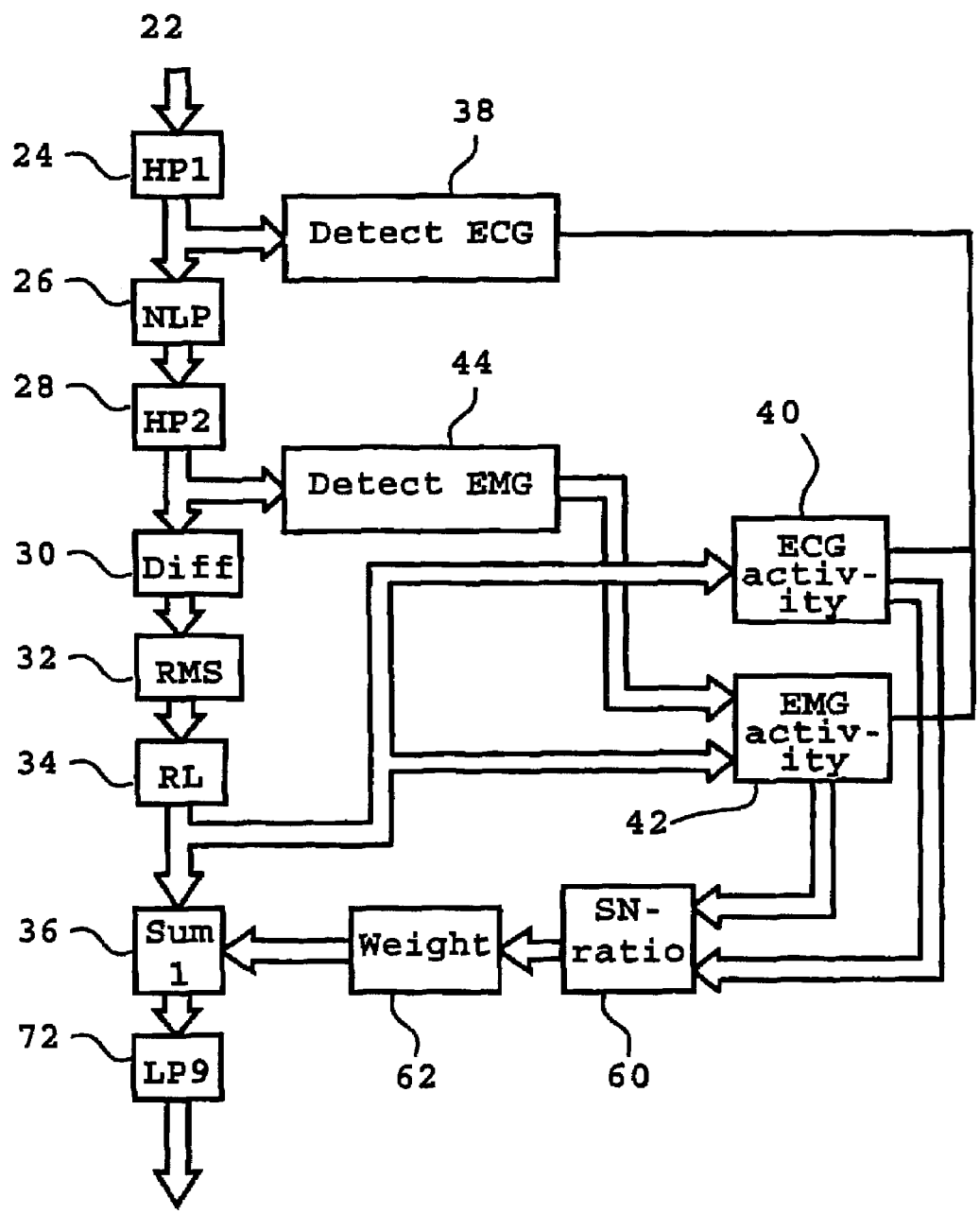
FIG. 4 is a flowchart describing the steps that are included in the signal treatment with the method according to the invention.

FIG. 4 shows a flowchart which describes the overall signal handling in the analysis unit 12. The general handling is as follows.

The raw signals from the sensors are input by a (multi-channel) input 22 and first pass a first high pass filter 24. The purpose of this is to filter away movement artifacts and other low-frequency interferences. The breaking frequency should be lower than 10 Hz.

In the next step, the signals are filtered in a non-linear low pass filter 26. The purpose of this is to smooth the signal when it has a high amplitude, which typically happens with the existence of EKG-signals. The breaking frequency should lie within an interval of about 50-700 Hz. Where in the interval the breaking frequency lies depends on the energy or the amplitude of the signal. Higher amplitude results in lower breaking frequency. The non-linear low pass filter 26 should even have a dynamic component, namely that the breaking frequency changes with a time constant.

Subsequently, the signals pass a second high pass filter 28. The purpose of the second high pass filter 28 is to select the frequency interval where the EMG-signal lies. The breaking frequency is therefore chosen to the lower regions of the bandwidth of the EMG-signal which is about 100 Hz.

The block 26 and 28 can be replaced with an adaptive band pass filter which is described in Swedish application 0303061-6 filed Nov. 19, 2003 and corresponding to Ser. No. 10/599,980 filed Mar. 26, 2007 and assigned to the same assignee as the present application, in connection with FIG. 6 in that application.

In the next step, nearby channels are differentiated from each other in a differentiator 30. The purpose of this is to remove ringing in the filter and is based on the assumption that nearby channels are correlated with reference to common-mode interferences.

Subsequently, the energy content of the signal is determined in an RMS-former 32 (Root Mean Square). To reduce any remaining spikes in EKG-signals (foremost related to the QRS-complex in the EKG-signal), the derivative of the signal from the RMS-former 32 is limited in a rate limit block 34.

In the next step, a summation is done in a summing unit 36. The purpose of the summing unit 36 is to weigh together the channels. This is done by multiplying the signals in the respective channels by a weight factor (see below), summing and normalizing the signals. In this connection the weighting factor can be squared to more selectively promote the channels with good signal-to-noise ratio. In principle, the summing unit 36 can be seen as a channel selector in which the channels that have the highest weighting factor are selected for use while the channels with poorer SNR can be allocated the value 0 in extreme cases.

The weighting factor for the respective channels is determined as follows.

After the first high pass filter 24, the signals in the channels are also passed to an EKG-detector 38. The purpose of the EKG-detector 38 is to establish the presence of the EKG-signals in the channels. If a single channel indicates the presence of an EKG-signal, an estimated EKG-activity is calculated for all of the channels. The determination of the estimated EKG-activity is done in a first calculation block 40. The output signal from the EKG-detector 38 is supplied to a second calculation block 42.

In the manner described above, the presence of EMG-signals can also be established. This is done in an EMG-detector 44, which is fed with the signal from the second high pass filter 28.

The output signals from the EMG-detector 44 are led to the second calculation block 42.

In addition to the signals mentioned above, the first calculation block 40 and the second calculation block 42 have a further input signal, namely the signal after the rate limit block 34.

The EKG detector 38 and the EMG detector 44 can be designed in different ways. In one formulation the EKG detector 38 is designed for each channel and thus for each signal which is received from an electrode, to detect if the EKG signal exceeds a limit value which is defined for the EKG signals. To make this comparison the raw signal is filtered in a band pass filter to take away the relevant frequency band for an EKG signal and the output signal from the band pass filter is compared with the set threshold. If the output signal is higher than the threshold the EKG signal is considered present.

In an alternative embodiment both the detectors 38, 44 are designed so that a first probability function $P_{EKG}$ is determined for each channel. $P_{EKG}$ indicates the probability that an EKG signal is present in the signal. A second probability function $P_{EMG}=1-P_{EKG}$ indicates the probability that an EMG signal is present in the signal.

The probability functions are calculated from a frequency analysis for the respective EKG and EMG signals.

Figure 5:
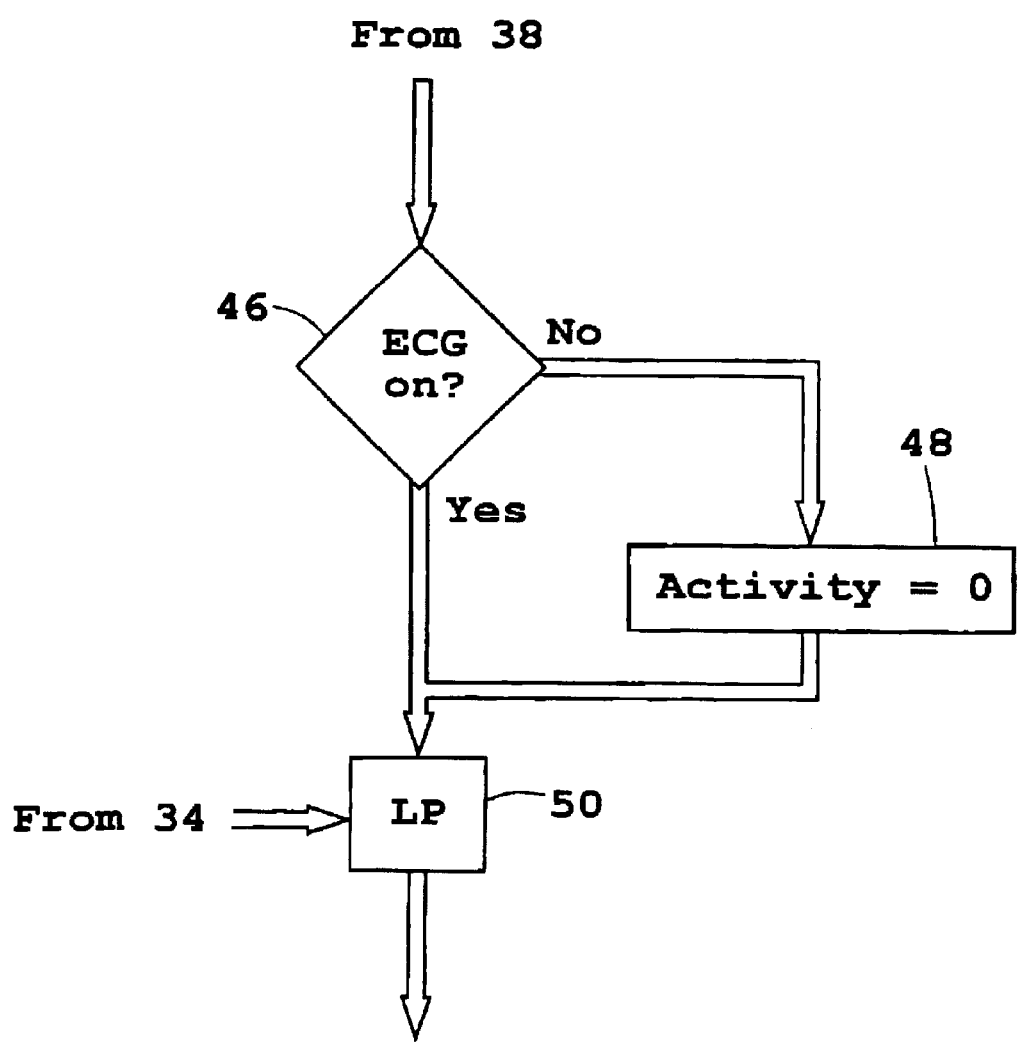
FIG. 5 is a flowchart showing how an ECG-activity is estimated with the method according to the invention.

The function of the first calculation block 40 is evident from FIG. 5. The signal from the EKG-detector 38 goes into a first decision block 46. Here it is established whether an EKG-signal is present in one of the channels (output yes) or not (output no). If there is no EKG-activity, the activity level is set to 0 in block 48 (estimated EKG-activity=0). If an EKG-signal is present in one of the channels, the estimated EKG-activity S is calculated for all the channels, which is done via a low pass filter 50, which also receives the filtered signal from the rate limit block 34. In the low pass filter 50, the D.C. voltage level for each channel is in principle determined, the filtered signal from rate limit block 34, (a breaking frequency of a few Hz can be accepted), which in that connection represents the estimated EKG-activity S.

Figure 6:
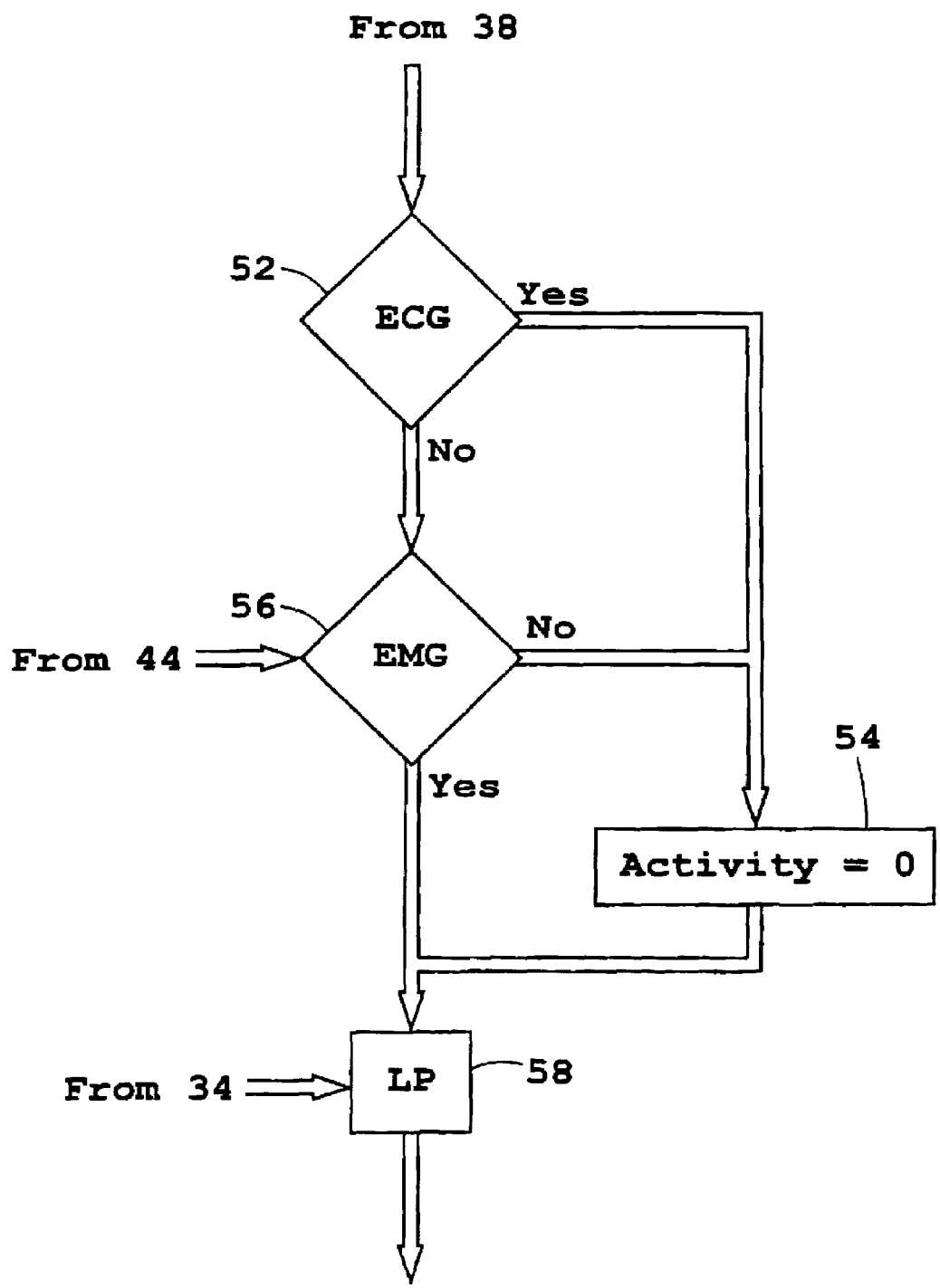
FIG. 6 is a flowchart showing how an EMG-activity is estimated with the method according to the invention.

The function of the second calculation block 42 is explained in FIG. 6. The signal from the EKG-detector 38 goes into a second decision block 52. If an EKG-signal exists (output yes), the estimated EMG-activity is set to 0 in block 54. If no EKG-signal exists (output no), it is investigated whether there exists some EMG-signal (from the EMG-detector 44) in a third decision block 56. If no EMG-signal exists (output no), the activity is set to 0 in the block 54. If EMG-signals exist, the estimated EMG-activity R is calculated by passing the signal, the filtered signal from Rate limit block 34, through a low pass filter 58.

Figure 7:
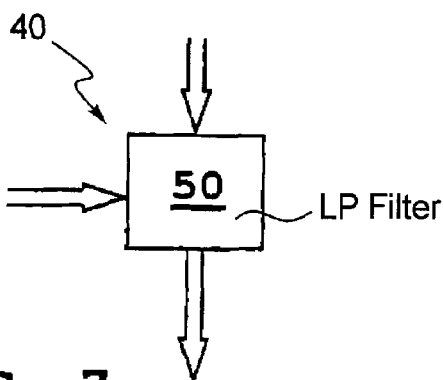
FIG. 7 and FIG. 8 are flowcharts showing, respectively, how an ECG activity and an EMG activity are estimated according to the method according to an alternative embodiment.
Figure 8:
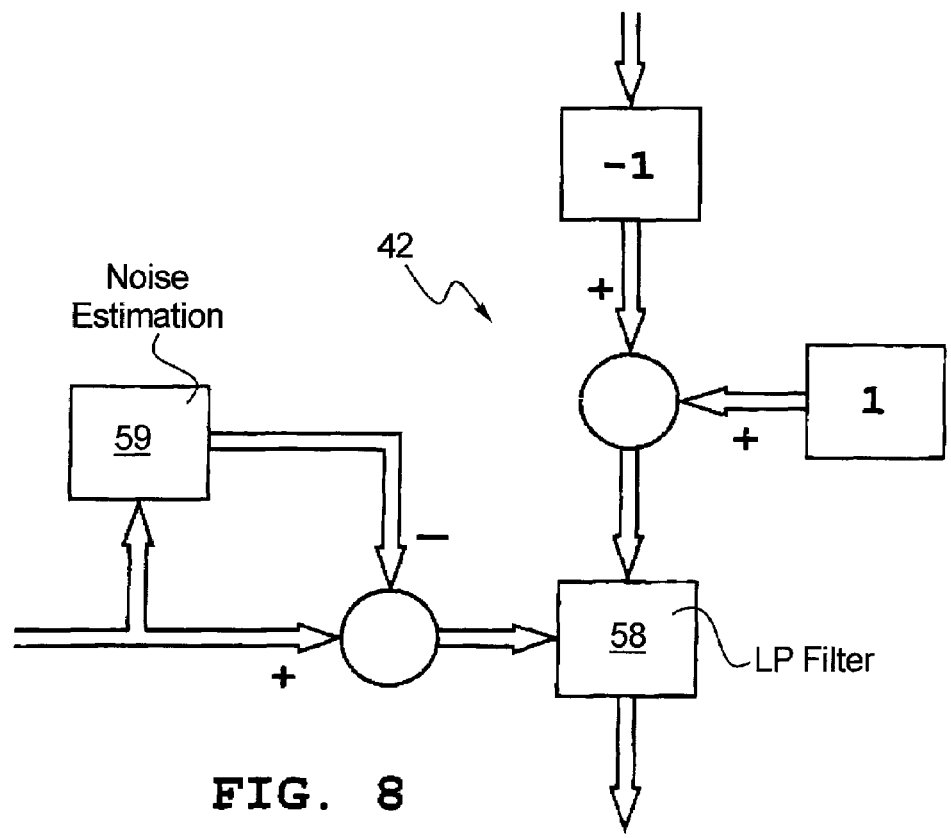

Another embodiment of the blocks 40 and 42 are shown in FIGS. 7 and 8, respectively.

FIG. 7 shows an alternative embodiment of the first calculation block 40 for estimating the EKG signal. From the rate limit block 34 a low pass filter 50 in the first calculation block 40 receives the filtered raw signal. From the EKG detector 38 it receives as previously the estimation of the presence of EKG signal. In contrast to the above-described embodiment the value which is received from the EKG detector is a probability function $P_{ECG}$ with a value between 0 and 1. The output signal from the calculation block 40 is an estimation of the effect contents in the EKG signal, which depends on the probability function.

FIG. 8 shows an alternative embodiment of the second calculation block 42 for estimating the EMG signal. The output signal from the EKG detector 38, $P_{ECG}$ is fed to a second calculation block 42 where the probability $1-P_{ECG}$ is fed to a low pass filter 58. The low pass filter 58 receives the filtered signal from the rate limit block 34. Before the filtered signal is fed to the low pass filter 58 the noise level in the signal is estimated in an estimating block 59 and cancelled from the signal. The output signal from the calculation block 42 is an estimation of the effect contents in the EMG signal, which depends on the mentioned probability function.

As shown, the embodiments shown in FIGS. 5 and 6 can be seen as a special case of that shown in FIGS. 7 and 8, where the probability $P_{ECG}$ can assume the value 0 or 1.

The estimated EMG-activity R and the estimated EKG-activity S are transferred to a SN-block 60 for determining a signal-to-noise ratio for each channel between the estimated EMG-activity R and the estimated EKG-activity S. The signal-to-noise ratio can be determined in different ways. One way to determine a signal-to-noise ratio T is by the quotient $$T = \frac{R}{R+S}$$

where R is the estimated EMG-activity and S is the estimated EKG-activity.

To promote channels with high estimated EMG-activity (regardless of interferences), it is advantageous to instead use the quotient $$T = \frac{R^2}{R+S}$$

Instead of $R^2$, $R^n$ can naturally be used, where n suitably is considerably larger or equal to 1.

Figure 9:
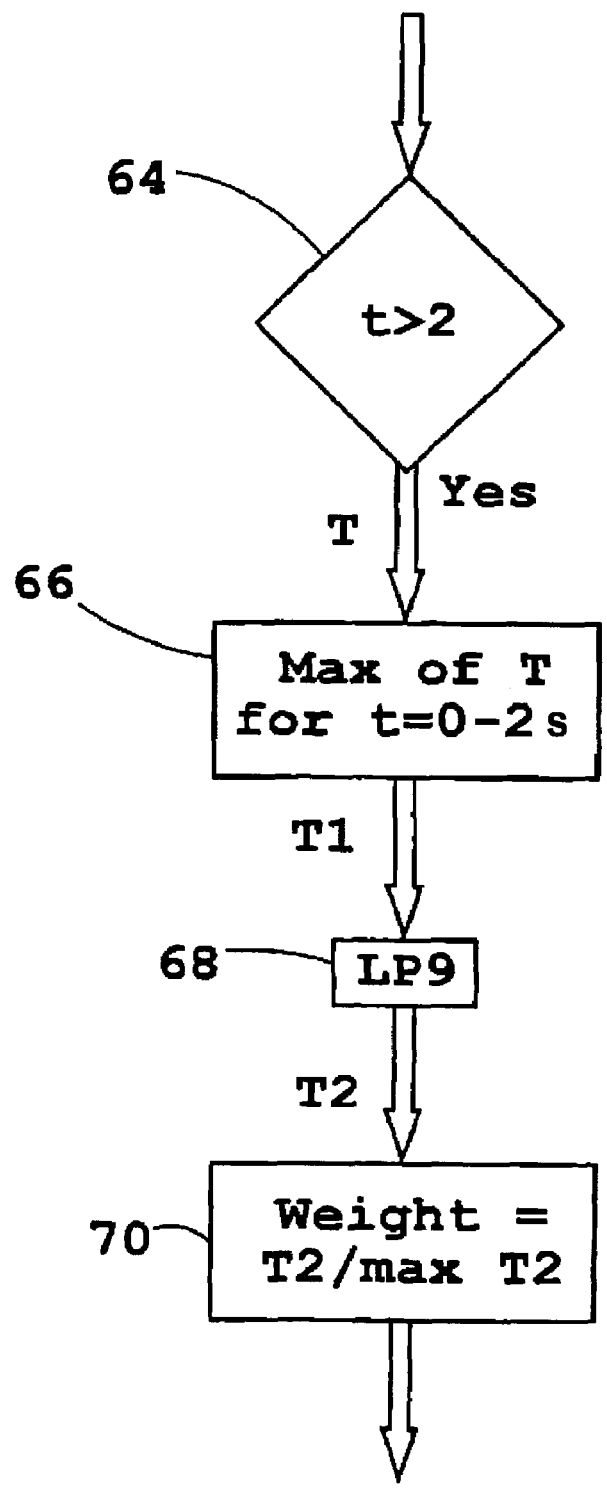
FIG. 9 is a flowchart showing how a weighing of signals on different signal channels can be obtained with the method according to the invention.

The signal-to-noise ratio is transferred to a weighting factor block 62, where a weighing is determined for each channel. The determinations in the weighting factor block 62 are shown in FIG. 9. A time block 64 counts time interval t, for example for a few seconds. In the example of FIG. 9, t must be longer than 2.5 seconds. During the respective time interval t, the maximum signal T1 is determined for the signal-to-noise ratio T from the SN-block 60 in a maximizing block 66. This maximum signal T1 is then filtered in a low pass filter 68. The filtered signal T2 then represents the base for the determination of a weighting factor for each channel in a calculation block 70. In this example, the weighting factor is set to $$\frac{T2}{\max T2}$$

where maxT2 is the maximum T2 for all the channels. In other words, the channels are normalized to the strongest signal-to-noise ratio of all the channels, such that the weighting factor for the respective channel receives a value between 0 and 1.

The determined weighting factors are then transferred to the summing unit 36 (FIG. 4), where handling is done as previously described. Finally, the signal can be smoothed in a low pass filter 72 and put out as a ready EMG-signal.

Preferably, a computer program is arranged in the analysis unit 12, which directs the function of the different blocks in the analysis unit according to the above.

In the method according to the present invention, the determination of weighting factors for the respective signal channels plays a major role. The numerical values given above, e.g. breaking frequencies and multiplication factors, are only examples and in no way exclude other values. Similarly, certain portions of the signal handling can be obtained in other ways without deviating from the invention.

Although modifications and changes may be suggested by those skilled in the art, it is the invention of the inventors to embody within the patent warranted heron all changes and modifications as reasonably and properly come within the scope of their contribution to the art.

We claim as our invention:

1. A computer-implemented method for extracting an EMG signal out of a raw signal, said raw signal being obtained by a plurality of electrodes adapted to interact with a patient to capture signals from the diaphragm of the patient, each electrode having an associated signal channel in which a raw signal is received from the associated electrode, said method comprising the steps of:

supplying the respective raw signals from said electrodes to a processor and, in said processor for each of said channels, automatically electronically determining a signal-to-noise ratio for the raw signal in that channel by automatically estimating a level of ECG activity in the raw signal, and automatically electronically estimating a level of EMG activity in the raw signal, and automatically electronically determining said signal-to-noise ratio based on the estimated level of ECG activity and the estimated level of EMG activity;

in said processor, for each of said channels, automatically electronically determining a weighting factor for that channel dependent on the signal-to-noise ratio of that channel;

in said processor, weighting the respective raw signals from the channels by the respective weighting factors determined for the channels, to obtain weighted raw signals, and summing the weighted raw signals to obtain a summed signal representing a total EMG signal in said raw signals; and emitting said summed signal as an output from said processor.

2. A method as claimed in claim 1 comprising:

In said processor, normalizing said summed signal representing the total EMG signal.

3. A method as claimed in claim 1 comprising automatically electronically calculating said signal-to-noise ratio according to the equation $R^n/(R+S)$, wherein R is the estimated level of EMG activity, S is the estimated level of ECG activity, and n is an integer greater than 1.

4. A method as claimed in claim 1 comprising estimating the level of ECG activity by filtering an estimated ECG signal out of the raw signal and comparing the estimated ECG signal with a threshold value.

5. A method as claimed in claim 1 comprising estimating the level of ECG activity comprises automatically electronically calculating a probability function indicating a probability that an ECG signal is included in the raw signal of the channel.

6. A method as claimed in claim 5 comprising estimating the level of ECG activity only if said probability function indicates a predetermined level of probability that an ECG signal is included in the raw signal of the channel.

7. A computerized device for extracting an EMG signal out of a raw signal, said raw signal being obtained by a plurality of electrodes adapted to interact with a patient to capture signals from the diaphragm of the patient, each electrode having an associated signal channel in which a raw signal is received from the associated electrode, said computerized device comprising:

an analysis unit supplied with the respective raw signals from said electrodes and programmed, for each of said channels, to automatically electronically determine a signal-to-noise ratio for the raw signal in that channel, by automatically estimating a level of ECG activity in the raw signal, and automatically electronically estimate a level of EMG activity in the raw signal, and automatically electronically determine said signal-to-noise ratio based on the estimated level of ECG activity and the estimated level of EMG activity and to automatically electronically determine a weighting factor for that channel dependent on the signal-to-noise ratio of that channel, and to weight the respective raw signals from the channels by the respective weighting factors determined for the channels, to obtain weighted raw signals, and to sum the weighted raw signals to obtain a summed signal representing a total EMG signal in said raw signals and to emit the summed signal as an output from the analysis unit.

8. A device as claimed in claim 7 wherein said analysis unit is programmed to normalize said summed signal representing the total EMG signal.

9. A device as claimed in claim 7 wherein said analysis unit is programmed to automatically electronically calculate said signal-to-noise ratio according to the equation $R^n/(R+S)$, wherein R is the estimated level of EMG activity, S is the estimated level of ECG activity, and n is an integer greater than 1.

10. A device as claimed in claim 7 wherein said analysis unit is programmed to estimate the level of ECG activity by filtering an estimated ECG signal out of the raw signal and comparing the estimated ECG signal with a threshold value.

11. A device as claimed in claim 7 wherein said analysis unit is programmed to estimate the level of ECG activity by automatically electronically calculating a probability function indicating a probability that an ECG signal is included in the raw signal of the channel.

12. A device as claimed in claim 11 wherein said analysis unit is programmed to estimate the level of ECG activity only if said probability function indicates a predetermined level of probability that an ECG signal is included in the raw signal of the channel.

13. A computer-readable medium encoded with a computer program loadable into a computer for extracting an EMG signal out of a raw signal, said raw signal being obtained by a plurality of electrodes adapted to interact with a patient to capture signals from the diaphragm of the patient, each electrode having an associated signal channel in which a raw signal is received from the associated electrode, said computer program comprising programming instructions causing said computer to:

for each of said channels, determine a signal-to-noise ratio for the raw signal in that channel by automatically estimating a level of ECG activity in the raw signal, and automatically electronically estimating a level of EMG activity in the raw signal, and automatically electronically determining said signal-to-noise ratio based on the estimated level of ECG activity and the estimated level of EMG activity;

for each of said channels, determine a weighting factor for that channel dependent on the signal-to-noise ratio of that channel; and weight the respective raw signals from the channels by the respective weighting factors determined for the channels, to obtain weighted raw signals, and sum the weighted raw signals to obtain a summed signal representing a total EMG signal in said raw signals.

14. A computer readable medium as claimed in claim 13 wherein said computer program causes said computer to is programmed to normalize said summed signal representing the total EMG signal.

15. A computer readable medium as claimed in claim 13 wherein said programming instructions cause said computer to calculate said signal-to-noise ratio according to the equation $R^n/(R+S)$, wherein R is the estimated level of EMG activity, S is the estimated level of ECG activity, and n is an integer greater than 1.

16. A computer readable medium as claimed in claim 13 wherein said programming instructions cause said computer to estimate the level of ECG activity by filtering an estimated ECG signal out of the raw signal and comparing the estimated ECG signal with a threshold value.

17. A computer readable medium as claimed in claim 13 wherein said programming instructions cause said computer to estimate the level of ECG activity by calculating a probability function indicating a probability that an ECG signal is included in the raw signal of the channel.

18. A computer readable medium as claimed in claim 17 wherein said programming instructions cause said computer to estimate the level of ECG activity only if said probability function indicates a predetermined level of probability that an ECG signal is included in the raw signal of the channel.

* * * * *